(12) United States Patent
Candau

(10) Patent No.: US 6,251,373 B1
(45) Date of Patent: *Jun. 26, 2001

(54) PHOTOPROTECTIVE/COSMETIC COMPOSITIONS COMPRISING BENZOTRIAZOLE, BISRESORCINYLTRIAZINE AND BENZOAZOLYL/BENZODIAZOLYL SUNSCREENS

(75) Inventor: Didier Candau, Bievres (FR)

(73) Assignee: Societe L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/503,942

(22) Filed: Feb. 14, 2000

(30) Foreign Application Priority Data

Feb. 12, 1999 (FR) .................................................. 99 01731

(51) Int. Cl.⁷ .............................. A61K 7/42; A61K 7/44; A61K 7/00; A61K 31/53
(52) U.S. Cl. ............................. 424/59; 424/60; 424/400; 424/401; 514/241
(58) Field of Search ............................... 424/59, 60, 400, 424/401; 514/241

(56) References Cited

U.S. PATENT DOCUMENTS 5,585,091 * 12/1996 Pelzer et al. ........................... 424/59
5,955,060 * 9/1999 Huglin et al. ........................... 424/59
5,962,452 * 10/1999 Haase et al. ........................... 514/241

FOREIGN PATENT DOCUMENTS

| 196 45 317 A1 | 5/1998 | (DE) . |
| 0 697 481 A2 | 2/1996 | (EP) . |
| WO 98/22447 | 5/1998 | (WO) . |
| WO 98/23252 | 6/1998 | (WO) . |

* cited by examiner

Primary Examiner—Shelley A. Dodson
(74) Attorney, Agent, or Firm—Burns, Doane, Swecker & Mathis, L.L.P.

(57) ABSTRACT

Topically applicable sunscreen/cosmetic compositions well suited for the synergistically enhanced photoprotection of human skin and/or hair against the damaging effects of UV-irradiation, particularly solar ratiation, comprise synergistically UV-photoprotecting effective amounts of each of (a) at least one benzotriazole compound, (b) at least one bisresorcinyltriazine compound and (c) at least one compound containing at least two benzoazolyl groups per molecule and/or at least one compound containing, per molecule, at least one benzodiazolyl group, formulated into a topically applicable, cosmetically acceptable vehicle, diluent or carrier therefor.

40 Claims, No Drawings

PHOTOPROTECTIVE/COSMETIC COMPOSITIONS COMPRISING BENZOTRIAZOLE, BISRESORCINYLTRIAZINE AND BENZOAZOLYL/BENZODIAZOLYL SUNSCREENS

CROSS-REFERENCE TO PRIORITY APPLICATION

This application claims priority under 35 U.S.C. §119 of FR-99/01731, filed Feb. 12, 1999, hereby expressly incorporated by reference.

BACKGROUND OF THE INVENTION

1. Technical Field of the Invention

The present invention relates to novel cosmetic compositions for topical application, for the photoprotection of the skin and/or hair against ultraviolet radiation (such compositions hereinafter simply designated "antisun," "sunscreen" or "photoprotective" compositions) and to the use of same for the cosmetic applications indicated above.

This invention more especially relates to the aforesaid sunscreen/cosmetic compositions comprising, formulated into a cosmetically acceptable vehicle, diluent or carrier therefor, a tripartite combination comprising (a) at least one specific benzotriazole compound, as a first screening agent, (b) at least one bisresorcinyltriazine compound, as a second screening agent, and (c), as a third screening agent, at least one compound containing at least two benzoazolyl functional groups or at least one compound containing at least one benzodiazolyl functional group, the said first, second and third screening agents being present in the subject compositions in proportions suitable for eliciting a synergistic effect with regard to the protection factors conferred.

2. Description of the Prior Art

It is known to this art that light radiation with wavelengths of from 280 nm to 400 nm promotes tanning of the human epidermis and that irradiation with wavelengths of from 280 to 320 nm, i.e., UV-B radiation, causes erythemas and skin burns which may be harmful to the development of natural tanning; this UV-B radiation must therefore be screened from the skin.

It is also known to this art that UV-A radiation, with wavelengths of from 320 to 400 nm, which causes tanning of the skin, can also adversely affect it, in particular in the case of sensitive skin or of skin continually exposed to solar radiation. UV-A rays cause, in particular, a loss in the elasticity of the skin and the appearance of wrinkles, resulting in premature aging. Such irradiation promotes the triggering of the erythemal reaction or accentuates this reaction in certain individuals and can even be the cause of phototoxic or photoallergic reactions. It is therefore desirable to also screen out UV-A radiation.

A wide variety of cosmetic compositions for the photoprotection (UV-A and/or UV-B) of human skin are known to this art.

These photoprotective/sunscreen compositions are typically emulsions of oil-in-water type (namely, a cosmetically acceptable vehicle, diluent or carrier comprising a continuous aqueous dispersing phase and a non-continuous oily dispersed phase) which contains, in various concentrations, one or more conventional lipophilic and/or hydrophilic organic screening agents capable of selectively absorbing harmful UV radiation. These screening agents (and their amounts) are selected according to the desired protection factor (the protection factor (PF) being expressed mathematically by the ratio of the irradiation time required to attain the erythemogenic threshold with the UV screening agent to the time required to attain the erythemogenic threshold without UV screening agent).

SUMMARY OF THE INVENTION

It has now surprisingly and unexpectedly been determined that the combination of three specific sunscreen compounds already per se known to this art provides synergistically active sunscreen compositions exhibiting markedly improved protection factors.

Briefly, the present invention features novel cosmetic compositions, in particular photoprotective/sunscreen compositions, comprising, in a cosmetically acceptable vehicle, diluent or carrier, (a) at least one specific benzotriazole compound, as a first screening agent, (b) at least one bisresorcinyltriazine compound, as a second screening agent, and (c), as a third screening agent, at least one compound containing at least two benzoazolyl functional groups and/or at least one compound containing at least one benzodiazolyl functional group, the said first, second and third screening agents advantageously being formulated into the subject compositions in a proportion eliciting a synergistic effect with regard to the sun protection factors conferred.

The present invention also features the use of the subject compositions in the production of cosmetic compositions suited for the protection of the skin and/or hair against the deleterious effects of ultraviolet radiation, in particular solar radiation.

This invention thus also features a cosmetic regime/regimen for the photoprotection of skin and/or hair against the damaging effects of ultraviolet radiation, in particular solar radiation, which essentially entails topically applying onto the skin/hair a photoprotecting amount of a composition in accordance herewith.

DETAILED DESCRIPTION OF BEST MODE AND SPECIFIC/PREFERRED EMBODIMENTS OF THE INVENTION

More particularly according to the present invention, novel cosmetic or dermatological compositions, in particular photoprotecting/sunscreen compositions, are provided which comprise, formulated into a cosmetically acceptable vehicle, diluent or carrier therefor:

(a) as a first screening agent, at least one benzotriazole compound having the structural formula (I):

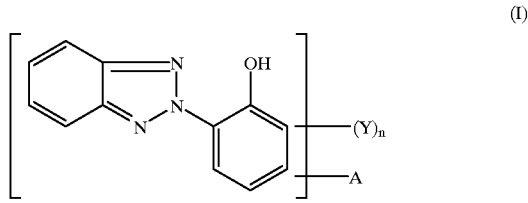

in which A is a hydrogen atom or a divalent radical —L—W—; the radicals Y, which may be identical or different, are each a $C_1$–$C_{10}$ alkyl radical, a halogen atom, a $C_1$–$C_{10}$ alkoxy radical or a sulfo group, with the proviso that, in the latter case, two adjacent Y radicals on the same aromatic nucleus can together form an alkylidenedioxy group in which the alkylidene moiety has 1 or 2 carbon atoms, with the further proviso that the Y radicals are other than a sulfo group when A is other than a hydrogen atom; n has the value 1, 2 or 3; L is a divalent radical having the following formula (II):

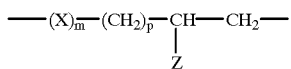

in which X is O or NH; Z is a hydrogen atom or a $C_1$–$C_4$ alkyl radical; n is an integer ranging from 0 to 3, inclusive; m is 0 or 1; p is an integer ranging from 1 to 10 inclusive; W is a radical having one of the following formulae (1), (2) or (3):

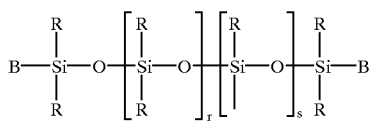

or

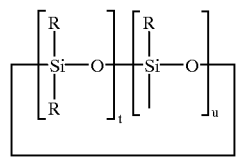

or

in which formulae the radicals R, which may be identical or different, are each a $C_1$–$C_{10}$ alkyl, phenyl or 3,3,3-trifluoropropyl radical, at least 80% by number of the R radicals being methyl radicals; the radicals B, which may be identical or different, are each an R radical or the V radical of the following formula:

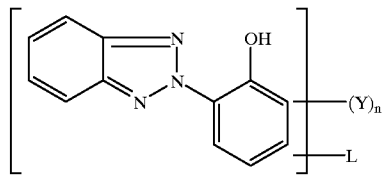

in which Y, n and L are as defined above; r is an integer ranging from 0 to 50, inclusive, and s is an integer ranging from 1 to 20, inclusive, and, if s=0, at least one of the two B radicals is a radical V; u is an integer ranging from 1 to 6, inclusive, and t is an integer ranging from 0 to 10, inclusive, with the proviso that t+u is equal to or greater than 3;

(b) as a second screening agent, at least one bisresorcinyltriazine compound; and (c) as the third screening agent, at least one compound containing at least two benzoazolyl functional groups per molecule or at least one compound containing, per molecule, at least one benzodiazolyl functional group, the said first, second and third screening agents being present in a proportion eliciting a synergistic effect with regard to the sun protection factors conferred.

By the term "containing at least two benzoazolyl functional groups" are intended, per molecule, at least two functional groups of the benzoxazolyl, benzothiazolyl or benzimidazolyl type.

By the term "containing at least one benzodiazolyl functional group" is intended, per molecule, a functional group of the benzodioxazolyl, benzodithiazolyl or benzodiimidazolyl type.

The benzotriazole compounds of formula (I) in accordance with the invention are screening agents already per se known to this art. They are described and prepared according to the syntheses illustrated in U.S. Pat. Nos. 4,316,033 and 4,328,346, and in EP-B-0,354,145, EP-B-0,392,883 and EP-B-0,660,701, hereby expressly incorporated by reference.

Exemplary nonsilicone compounds of formula (I) wherein A is a hydrogen atom include:

2-(2'-hydroxy-5'-methylphenyl)benzotriazole (n=1 and Y=$CH_3$), such as the product marketed under the trademark Uvazol P by Enichem Synth or the product marketed under the trademark Tinuvin P by Ciba-Geigy;

2-(2'-hydroxy-3'-butyl-5'-methylphenyl)benzotriazole (n=2 and Y=$CH_3$ and —C($CH_3$)$_3$), such as the product marketed under the trademark Uvazol 236 by Enichem Synth;

2-(2'-hydroxy-5'-(t-octyl)phenyl)benzotriazole (n=1 and Y=—C($CH_3$)$_2$—$CH_2$—C($CH_3$)$_3$), such as the product marketed under the trademark Uvazol 311 by Enichem Synth;

2-(2'-hydroxy-3'-(sec-butyl)-5'-sulfoophenyl)-benzotriazole (n=2 and Y=$SO_3H$, Y=—CH($CH_3$)—$CH_2$—$CH_3$), such as the product marketed under the trademark Cibafast by Ciba-Geigy.

In the case of the silicone compounds of formula (I) wherein A is a divalent radical —L—W—, in the definition of the formulae (1), (2) and (3) as defined above, the alkyl radicals can be linear or branched and advantageously are selected from among methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The preferred R alkyl radicals according to the invention are the methyl, ethyl, propyl, n-butyl, n-octyl and 2-ethylhexyl radicals. Even more preferably, the R radicals are all methyl radicals.

For the silicone compounds of formula (I) wherein A is a divalent radical —L—W—, it is preferable to employ those in which W corresponds to the formula (1), namely, linear-chain diorganosiloxanes.

More particularly preferred among the linear diorganosiloxanes according to the present invention, are statistical derivatives or well-defined block derivatives satisfying at least one and more preferably all of the following conditions:

R is alkyl and more preferably is methyl,

B is alkyl and more preferably is methyl, r ranges from 0 to 15, inclusive; s ranges from 1 to 5, inclusive, n is not zero and preferably is equal to 1 and Y is then selected from among methyl, tert-butyl or $C_1$–$C_4$ alkoxy radicals, Z is hydrogen or methyl, m=0 or [m=1 and X=0], p is equal to 1.

As derived from the formula (I) given above, the bonding or linking of the —(X)$_m$—(CH$_2$)$_p$—CH(Z)—CH$_2$—radical to the benzotriazole nucleus, which therefore provides the connection of the benzotriazole unit to the silicon atom of the silicone chain, can, according to the present invention, be at any of the available positions or sites presented by the two aromatic nuclei of the benzotriazole:

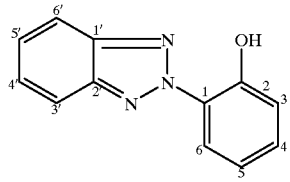

This linking or bonding preferably is at the 3-, 4- or 5-position (aromatic nucleus bearing the hydroxyl functional group) or 4'-position (benzene nucleus adjacent to the triazole ring) and more preferably still at the 3-, 4- or 5-position. In a preferred embodiment of the invention, the linking is via the 3-position.

Likewise, the linking of the Y substituent unit can be at any of the other positions available in the benzotriazole. However, this linking preferably is at the 3-, 4-, 4'-, 5- and/or 6-position. In a preferred embodiment of the invention, the linking is at the 5-position.

One family of compounds which is particularly suitable for the invention is that having the following structural formula:

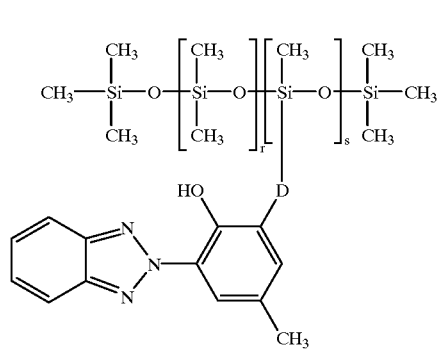

(I')

wherein $0 \leq r \leq 15$, preferably $0 \leq r \leq 10$, $1 \leq s \leq 5$, preferably $1 \leq s \leq 3$, and in which D is a divalent radical:

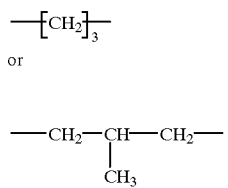

In a particularly preferred embodiment of the invention, the benzotriazole silicone has the structural formula (I') in which:

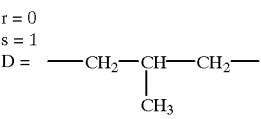

In another particularly preferred embodiment of the invention, the benzotriazole silicone has the structural formula (I') in which:

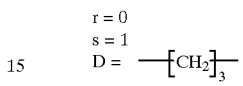

The benzotriazole compounds of formula (I) are advantageously present in amounts ranging from 0.1% to 15%, preferably from 0.2% to 10%, by weight, always with respect to the total weight of the composition; preferably, the overall content of the mixture of the first sunscreen (a) and the second sunscreen (b) does not exceed 15% of the total weight of the final composition.

The bisresorcinyltriazine derivatives compounds according to the invention are preferably selected from among those having the following structural formula:

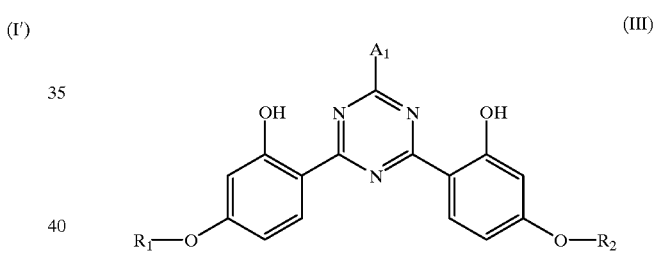

(III)

in which (i) the $R_1$ and $R_2$ radicals, which may be identical or different, are each a $C_3$-$C_{18}$ alkyl radical, a $C_2$-$C_{18}$ alkenyl radical, or a residue of formula —$CH_2$—CH(OH)—$CH_2$—$OT_1$ wherein $T_1$ is a hydrogen atom or a $C_1$-$C_8$ alkyl radical; or (ii) the $R_1$ and $R_2$ radicals, which again may be identical or different, can each also be a residue of the following formula (4):

(4)

in which $m_1$ is a number ranging from 1 to 3; $R_3$ is a hydroxyl group, a $C_1$-$C_5$ alkyl radical which is unsubstituted or substituted by one or more hydroxyl groups, a $C_1$-$C_5$ alkoxy radical, an amino group, a mono- or di($C_1$-$C_5$)alkylamino radical, a metal cation M, or a residue having one of the following formulae (5) to (10):

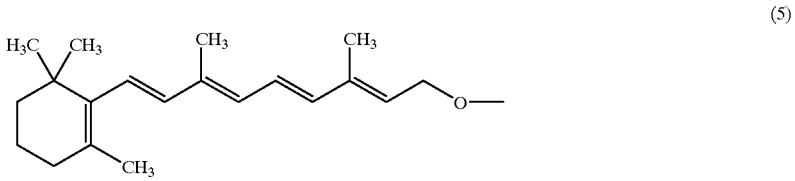
(5)

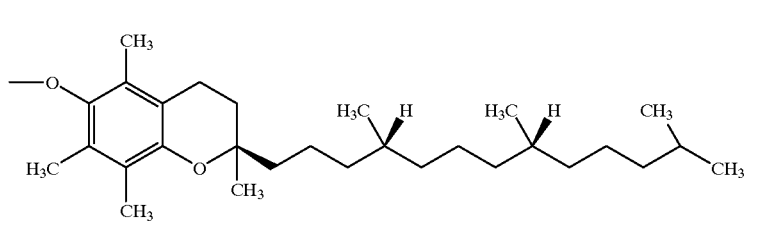
(6)

(7)

(8)

(9)

(10)

in which the $R_4$, $R_5$ and $R_6$ radicals, which may be identical or different, are each a $C_1$–$C_{14}$ alkyl radical which is unsubstituted or substituted by one or more hydroxyl groups; $R_7$ is a hydrogen atom, a metal cation M, a $C_1$–$C_5$ alkyl radical, or a residue of formula —$(CH_2)_{m_2}$—$OT_1$ where $m_2$ is a number ranging from 1 to 4 and $T_1$ is as defined above; or (iii) the $R_1$ and $R_2$ radicals, which again may be identical or different, can also each be a residue of the following formula (11):

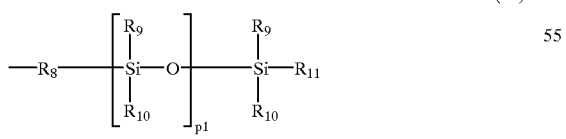
(11)

in which $R_8$ is a covalent bond, a linear or branched $C_1$–$C_4$ alkyl radical or a residue of formula —$C_{m_4}H_{2m_4}$— $C_{m_4}H_{2m_4}$—O— wherein $m_4$ is a number ranging from 1 to 4; $p_1$ is a number ranging from 0 to 5; the $R_9$, $R_{10}$ and $R_{11}$ radicals, which may be identical or different, are each a $C_1$–$C_{18}$ alkyl radical, a $C_1$–$C_{18}$ alkoxy radical, or a residue of the formula:

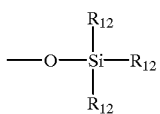
(12)

wherein $R_{12}$ is a $C_1$–$C_5$ alkyl radical; $A_1$ is a residue corresponding to one of the following formulae:

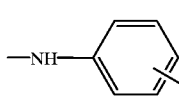
(10)

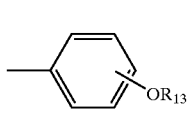
(13)

-continued (14)

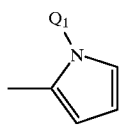

(15)

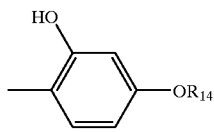

in which $R_7$ is as defined above; $R_{13}$ is a hydrogen atom, a $C_1$–$C_{10}$ alkyl radical, a radical of formula —$(CH_2CHR_{16}$—$O)_{n1}R_7$ wherein $n_1$ is a number ranging from 1 to 16 and $R_{16}$ is a hydrogen atom or a methyl radical, or a residue of formula —$CH_2$—$CH(OH)$—$CH_2OT_1$ wherein $T_1$ is as defined above; $Q_1$ is a $C_1$–$C_{18}$ alkyl radical; $R_{14}$ is a radical having the formula (4):

(4)

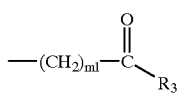

as defined above. In the above formulae (III) and (4) to (15):

(a) the alkyl radicals are linear or branched and can be selected, for example, from among methyl, ethyl, n-propyl, isopropyl, n-butyl, sec-butyl, tert-butyl, amyl, isoamyl, tert-amyl, heptyl, octyl, isooctyl, nonyl, decyl, undecyl, dodecyl, tetradecyl, pentadecyl, hexadecyl, heptadecyl or octadecyl;

(b) the $C_2$–$C_{18}$ alkenyl radicals can be selected, for example, from among allyl, methallyl, isopropenyl, 2-butenyl, 3-butenyl, isobutenyl, n-penta-2,4-dienyl, 3-methylbut-2-enyl, n-oct-2-enyl, n-dodec-2-enyl, isodedecenyl or n-octadec-4-enyl;

(c) the alkoxy radicals are linear or branched and can be selected, for example, from among methoxy, ethoxy, n-propoxy, isopropoxy, n-butoxy, sec-butoxy, tert-butoxy, amyloxy, isoamyloxy or tert-amyloxy;

(d) the mono- or dialkylamino radicals can be selected, for example, from among methylamino, ethylamino, propylamino, n-butylamino, sec-butylamino, tert-butylamino, pentylamino, dimethylamino, diethylamino, dibutylamino or methylethylamino;

(e) the metal cations M are alkali metal, alkaline earth metal, or metal cations selected, for example, lithium, potassium, sodium, calcium, magnesium, copper or zinc.

The bisresorcinyltriazine compounds of formula (III) of the invention are screening agents per se known to this art. They are described and prepared according to the syntheses illustrated in EP-A-0,775,698 and EP-A-0,878,469, hereby expressly incorporated by reference.

Exemplary bisresorcinyltriazine compounds of formula (III) are those in which the $A_1$ radical is para-methoxyphenyl or 4-ethoxyphenyl and the $R_1$ and $R_2$ radicals, which may be identical or different, are each a radical having the structure:

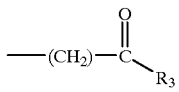

in which $R_3$ is selected from among:
tert-butyloxy;
OH;
OM, wherein M is an alkali metal or alkaline earth metal cation, or a cation selected from among copper, magnesium or zinc;
a group having the structure:

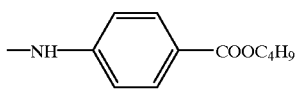

a group having the structure $O^-N^+(CH_2CH_2OH)_3$;
a group having the structure:

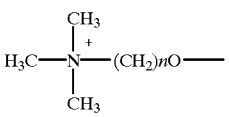

wherein n ranges from 2 to 16;
a group having the structure:

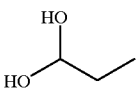

or a group having the structure:

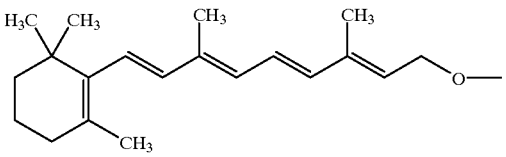

Also exemplary are bisresorcinyltriazine compounds having the formula (III) in which the $A_1$ radical is para-hydroxyphenyl and the $R_1$ and $R_2$ radicals simultaneously are each a group having the structure:

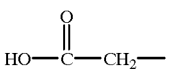

Representative compounds of formula (III) are:
2,4-bis{[4-(2-ethylhexyloxy)-2-hydroxy]phenyl}-6-(4-methoxyphenyl)-1,3,5-triazine;
2,4-bis{[4-(3-(2-propyloxy)-2-hydroxypropyloxy)-2-hydroxy]phenyl}-6-(4-methoxyphenyl)-1,3,5-triazine;
2,4-bis{[4-(2-ethylhexyloxy)-2-hydroxy]phenyl}-6-[4-(2-methoxyethyloxycarbonyl)phenylamino]-1,3,5-triazine;
2,4-bis{[4-(tris(trimethylsiloxy)silylpropyloxy)-2-hydroxy]phenyl}-6-(4-methoxyphenyl)-1,3,5-triazine;
2,4-bis{[4-(2"-methylpropenyloxy)-2-hydroxy]phenyl}-6-(4-methoxyphenyl)-1,3,5-triazine;

2,4-bis{[4-(1',1',1',3',5',5',5'-heptamethyltri-siloxy-2"-methylpropyloxy)-2-hydroxy]phenyl}-6-(4-methoxyphenyl)-1,3,5-triazine;

2,4-bis{[4-(3-(2-propyloxy)-2-hydroxypropyloxy)-2-hydroxy]phenyl}-6-[4-(ethoxycarbonyl)phenylamino]-1,3,5-triazine;

2,4-bis{[4-(2-ethylhexyloxy)-2-hydroxy]phenyl}-6-(1-methylpyrrol-2-yl)-1,3,5-triazine.

Particularly preferred bisresorcinyltriazine compounds according to the invention include:

2,4-bis{[4-(2-ethylhexyloxy)-2-hydroxy]phenyl}-6-(4-methoxyphenyl)-1,3,5-triazine;

2,4-bis{[4-(tris(trimethylsiloxy)silylpropyloxy)-2-hydroxy]phenyl}-6-(4-methoxyphenyl)-1,3,5-triazine;

2,4-bis{[4-(1',1',1',3',5',5',5'-heptamethyltrisiloxy-2"-methylpropyloxy)-2-hydroxy]phenyl}-6-(4-methoxyphenyl)-1,3,5-triazine.

The bisresorcinyltriazine sunscreen or sunscreens are advantageously present in the compositions according to the invention at a concentration ranging from 0.1% to 15%, preferably from 0.2% to 10%, by weight with respect to the total weight of the composition.

Preferred compounds containing at least two benzoazolyl groups in accordance with the invention are those having the following structural formula (IV):

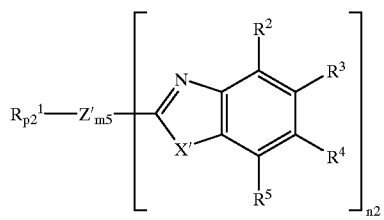

(IV)

in which Z' is an organic residue with a valency of ($p_2+n_2$) comprising one or more double bonds which are positioned such that the double bond completes the system of double bonds of at least two benzoazolyl groups as depicted within the brackets, in order to form a completely conjugated structural unit; X' is S, O or $NR^6$; $R^1$ is a hydrogen atom, a $C_1$–$C_{18}$ alkyl radical, a $C_1$–$C_4$ alkoxy radical, a $C_5$–$C_{15}$ aryl radical, a $C_2$–$C_{18}$ acyloxy radical, $SO_3Y'$ or $COOY'$; the $R^2$, $R^3$, $R^4$ and $R^5$ radicals, which may be identical or different, are each a nitro group or a radical $R^1$; $R^6$ is a hydrogen atom, a $C_1$–$C_4$ alkyl radical, or a $C_1$–$C_4$ hydroxyalkyl radical; Y' is a hydrogen atom, Li, Na, K, $NH_4$, 1/2Ca, 1/2Mg, 1/3Al, or a cation resulting from the neutralization of a free acid group by a nitrogenous organic base; $M_5$ is 0 or 1; $n_2$ is a number ranging from 2 to 6; $p_2$ is a number ranging from 1 to 4; with the proviso that $p_2+n_2$ does not exceed the value 6.

The compounds of formula (IV) according to the invention are water-soluble UV-A screening agents described in EP-A-0,669,323. They are also described and prepared according to the syntheses illustrated in U.S. Pat. No. 2,463,264 and EP-A-0,669,323, hereby expressly incorporated by reference.

Preferred compounds of formula (IV) of the invention are those in which the Z' group is selected from among:

(a) an unsaturated linear aliphatic $C_2$–$C_6$ hydrocarbonaceous radical which can be interrupted by a $C_5$–$C_{12}$ aryl radical or a $C_4$–$C_{10}$ heteroaryl radical, such as, for example: —CH=CH—, —CH=CH—CH=CH— or

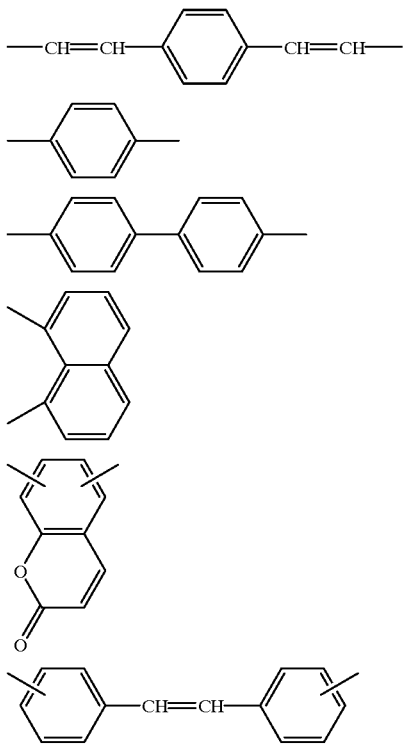

(c) a $C_3$–$C_{10}$ heteroaryl radical, such as, for example, the following groups:

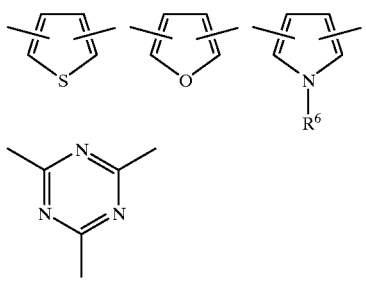

wherein $R^6$ is as defined above, with the proviso that said Z' radicals as defined in paragraphs (a), (b) and (c) may be substituted by $C_1$–$C_6$ alkyl, $C_1$–$C_6$ alkoxy, phenoxy, hydroxyl, methylenedioxy or amino radicals, the amino radicals optionally being substituted by one or two $C_1$–$C_5$ alkyl radicals.

Exemplary compounds of formula (IV) according to the invention include those having the following structural formulae, and salts thereof:

Compound 1

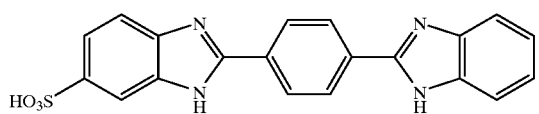

Compound 2
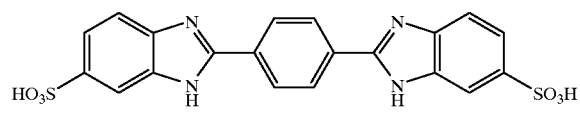
Compound 3
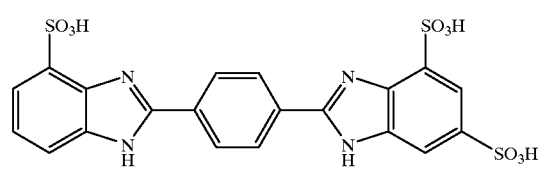
Compound 4
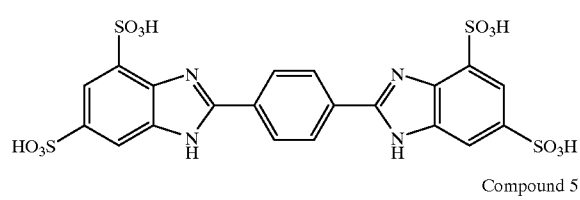
Compound 5
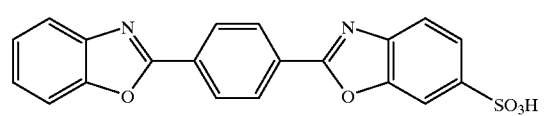
Compound 6
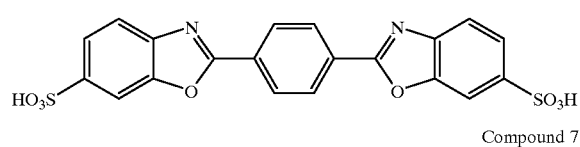
Compound 7
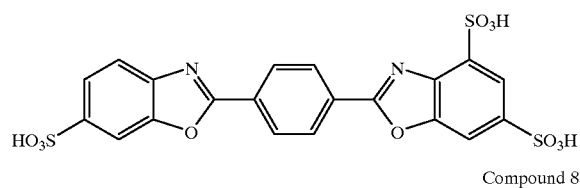
Compound 8
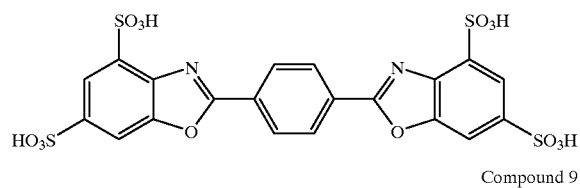
Compound 9
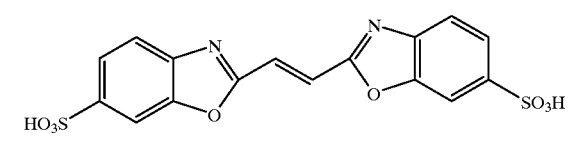
Compound 10
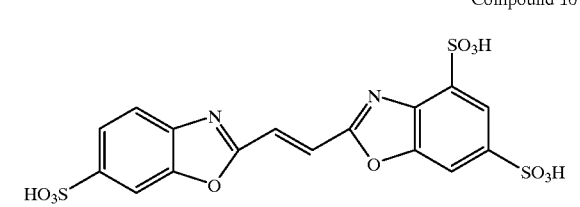
Compound 11
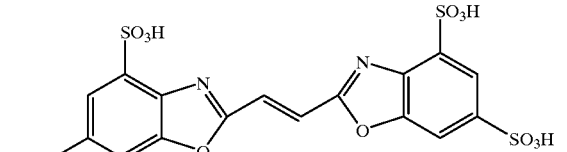
Compound 12
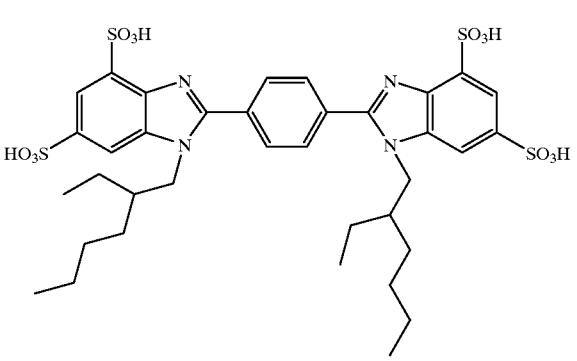
Compound 13
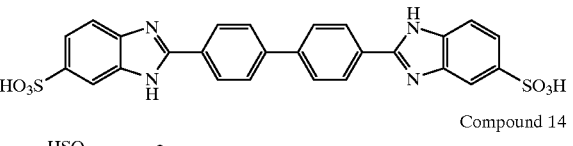
Compound 14
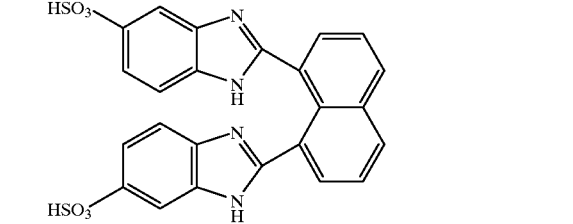
Compound 15
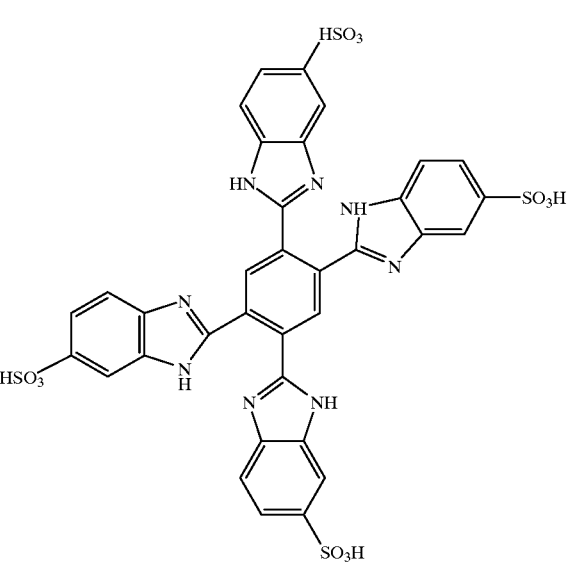

Compound 16
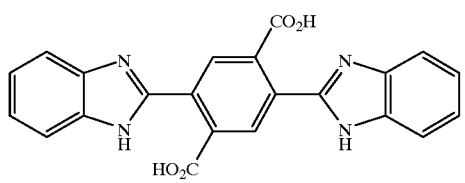

Compound 17
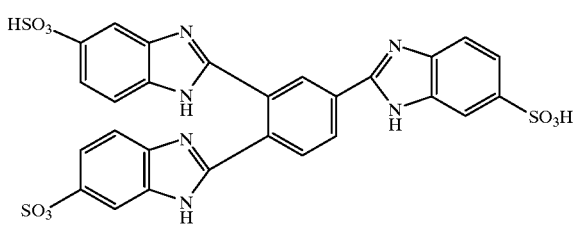

Compound 18
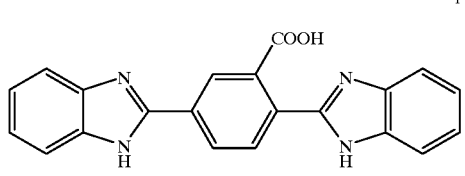

Compound 19
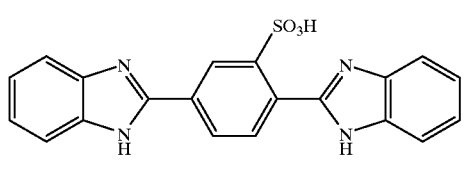

Compound 20
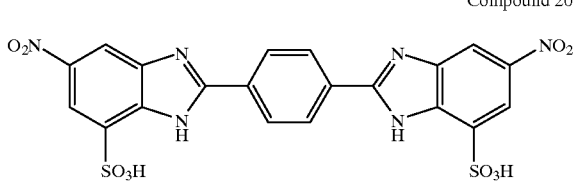

Compound 21
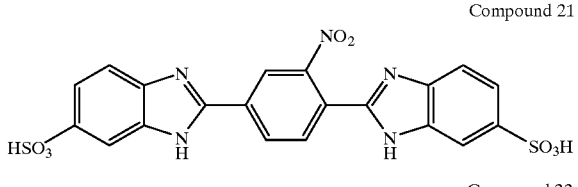

Compound 22
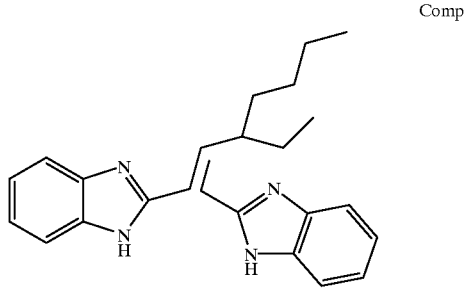

Compound 23
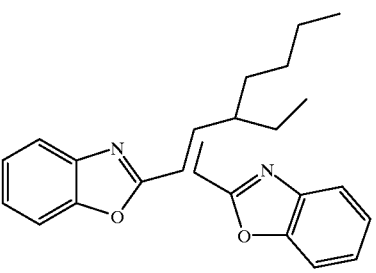

Compound 24
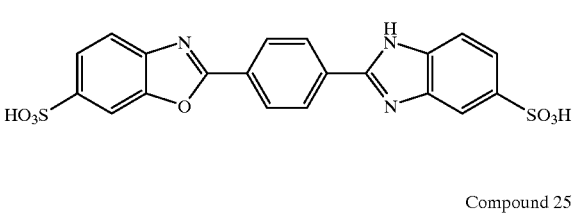

Compound 25
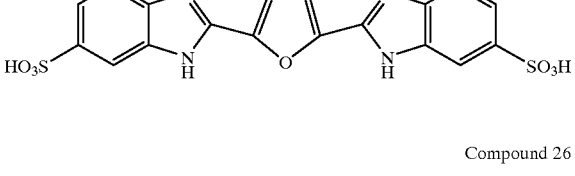

Compound 26
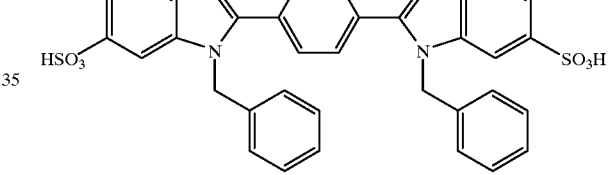

Compound 27
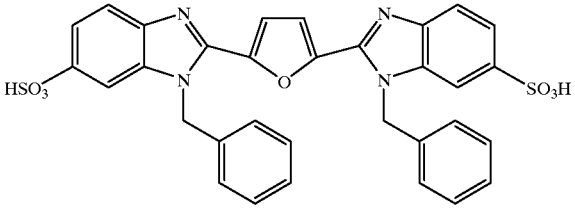

Among these compounds, preferred are 1,4-bis(benzimidazolyl)-phenylene-3,3',5,5'-tetrasulfonic acid (Compound 4) and salts thereof, having the following structural formula:

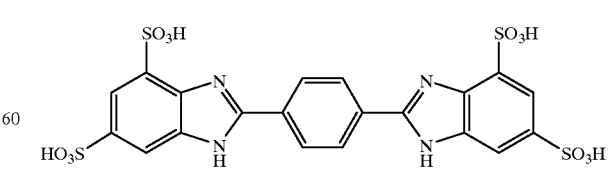

Also exemplary of the subject compounds containing at least two benzoazolyl groups, are the following compounds and salts thereof:

Compound 28

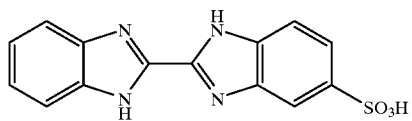

Compound 29

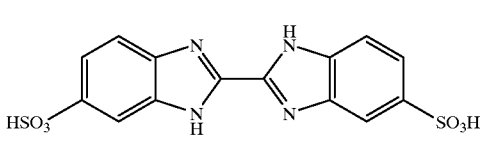

Compound 30

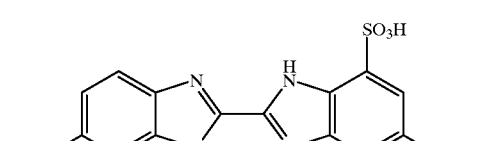

Compound 31

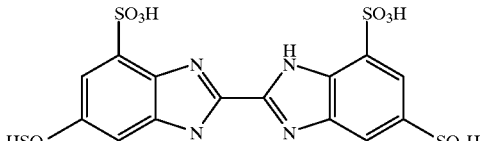

Exemplary compounds containing at least one benzodiazolyl group according to the invention, are the following compounds and salts thereof:

Compound 32

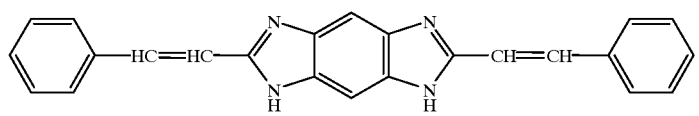

Compound 33

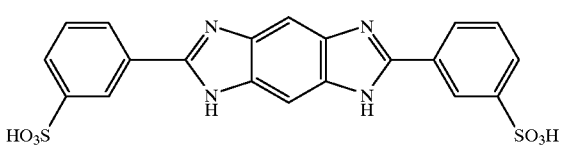

Compound 34

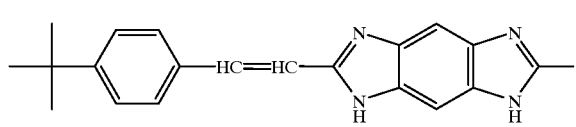

The compound or compounds containing 5 benzoazolyl or benzodiazolyl groups in accordance with the invention are advantageously present in the subject compositions at a concentration ranging from 0.1% to 15%, preferably from 0.2% to 10%, by weight with respect to the total weight of the composition.

As indicated above, in a characteristic embodiment of the present invention, the subject three types of sunscreens are each present in the final composition in respective proportions such that a substantial and significant synergistic effect is obtained with regard to the protection factor conferred by the resulting combination.

In addition and generally, it should be noted that the concentrations and ratios of benzotriazole compounds of formula (I), bisresorcinyltriazine compounds and compounds containing benzoazolyl or benzodiazolyl groups as described above are selected such that the sun protection factor of the final composition is preferably at least 2.

In another preferred embodiment of the present invention, the cosmetically acceptable medium (vehicle, diluent or carrier) in which the various screening agents are present is an emulsion of oil-in-water type.

The sunscreen/antisun cosmetic compositions according to the invention can, of course, contain one or more additional hydrophilic or lipophilic sunscreens which are active in the UV-A and/or UV-B regions (absorbers), other than the two screening agents indicated above. These additional screening agents are advantageously selected from among cinnamic derivatives, salicylic derivatives, camphor derivatives, triazine derivatives, such as those described in EP-863,145, EP-517,104, EP-570,838 and EP-796,851, benzophenone derivatives, dibenzoylmethane derivatives, β,β-diphenylacrylate derivatives, benzimidazole derivatives other than those described above, p-aminobenzoic acid derivatives, or screening polymers and screening silicones, such as those described in WO-93/04665.

Exemplary such additional sunscreens which are active in the UV-A and/or UV-B ranges include:

p-aminobenzoic acid;
oxyethylenated (25 mol) p-aminobenzoate;
2-ethylhexyl p-dimethylaminobenzoate;
N-oxypropylenated ethyl p-aminobenzoate;
glycerol p-aminobenzoate;
homomenthyl salicylate;
2-ethylhexyl salicylate;
triethanolamine salicylate;
4-isopropylbenzyl salicylate;
4-tert-butyl-4'-methoxydibenzoylmethane;
4-isopropyldibenzoylmethane;
2-ethylhexyl 4-methoxycinnamate;
methyl diisopropylcinnamate;
isoamyl 4-methoxycinnamate;
diethanolamine 4-methoxycinnamate;
menthyl anthranilate;
2-ethylhexyl 2-cyano-3,3-diphenylacrylate;
ethyl 2-cyano-3,3-diphenylacrylate;
2-phenylbenzimidazole-5-sulfonic acid and its salts;
3-(4'-trimethylammonio)benzylidenebornan-2-one methyl sulfate;

benzene-1,4-di(3-methylidene-10-camphorsulfonic acid) and its salts;
urocanic acid;
2-hydroxy-4-methoxybenzophenone;
2-hydroxy-4-methoxybenzophenone-5-sulfonate;
2,4-dihydroxybenzophenone;
2,2',4,4"-tetrahydroxybenzophenone;
2,2'-dihydroxy-4,4'-dimethoxybenzophenone;
2-hydroxy-4-(n-octoxy)benzophenone;
2-hydroxy-4-methoxy-4'-methylbenzophenone;
α-(2-oxoborn-3-ylidene)toluene-4-sulfonic acid and its salts;
3-(4'-sulfobenzylidene)bornan-2-one and its salts;
3-(4'-methylbenzylidene)-d,l-camphor;
3-benzylidene-d,l-camphor;
2,4,6-tris[p-(2'-ethylhexyl-1'-oxycarbonyl)anilino]-1,3,5-triazine;
2-[p-(tert-butylamido)anilino]-4,6-bis[(p-(2'-ethyl-hexyl-1'-oxycarbonyl)anilino]-1,3,5-triazine; the polymer of N-[(2- and 4-)][(2-oxoborn-3-ylidene)-methyl]benzyl] acrylamide; polyorganosiloxanes comprising a malonate functional group.

The compositions of this invention can also contain active agents for the artificial tanning and/or browning of the skin (self-tanning agents), such as, for example, dihydroxyacetone (DHA).

The cosmetic compositions of this invention can also contain pigments or alternatively nanopigments (mean size of the primary particles: generally ranging from 5 nm to 100 nm, preferably from 10 nm to 50 nm) comprising metal oxides which are coated or uncoated, such as, for example, titanium dioxide (amorphous or crystallized in the rutile and/or anatase form), iron oxide, zinc oxide, zirconium oxide or cerium oxide nanopigments which are all UV photoprotective agents well known per se. Furthermore, alumina and/or aluminum stearate are conventional coating agents. Such coated or uncoated metal oxide nanopigments are described, in particular, in EP-A-0,518,772 and EP-A-0,518,773.

The compositions of the invention can additionally contain conventional cosmetic additives and adjuvants selected, in particular, from among fatty substances, organic solvents, thickeners, softeners, antioxidants, opacifiers, stabilizers, emollients, hydroxy acids, antifoaming agents, moisturizing agents, vitamins, fragrances, preservatives, surfactants, fillers, sequestering agents, polymers, propellants, basifying or acidifying agents, dyes, colorants, or any other ingredient commonly formulated into cosmetics, in particular in the production of antisun/sunscreen compositions formulated as emulsions.

Exemplary fatty substances include oils or waxes or their mixtures and they also comprise fatty acids, fatty alcohols and fatty acid esters. The oils are selected from among animal, vegetable, mineral or synthetic oils and in particular from liquid petrolatum, liquid paraffin, volatile or non-volatile silicone oils, isoparaffins, poly-α-olefins, or fluorinated and perfluorinated oils. Likewise, the waxes are advantageously selected from among animal, fossil, vegetable, mineral or synthetic waxes per se well known to this art.

Exemplary organic solvents include the lower alcohols and polyols.

The thickeners are advantageously selected from among crosslinked homopolymers of acrylic acid, or modified or unmodified guar gums and celluloses, such as hydroxypropylated guar gum, methylhydroxyethyl-cellulose, hydroxypropylmethyl cellulose or hydroxyethylcellulose.

One skilled in this art will of course take care to select this or these optional additional compounds and/or their amounts such that the advantageous properties, in particular the sun protection factors, intrinsically provided by the ternary combination in accordance with the invention are not, or are not substantially, adversely affected by the envisaged addition or additions.

The compositions of the invention are easily formulated according to techniques well known to this art, in particular those suited for the formulation of emulsions of oil-in-water or water-in-oil type.

Such compositions can be provided, in particular, in the form of a simple or complex emulsion (O/W, W/O, O/W/O or W/O/W), such as a cream, a milk, a gel or a cream gel, a lotion, an ointment, a powder or of a solid tube or stick and can optionally be packaged as an aerosol and provided in the form of a foam or spray.

When formulated as an emsulsion, the aqueous phase thereof can comprise a non-ionic vesicular dispersion prepared according to known techniques (Bangham, Standish and Watkins, *J. Mol. Biol.*, 13, 238 (1965), FR-2,315,991 and FR-2,416,008).

The cosmetic compositions of the invention are useful for protecting the human epidermis or the hair against ultraviolet rays, as an antisun/sunscreen composition or as a makeup product.

When the cosmetic compositions according to the invention are used for the photoprotection of the human epidermis against UV irradiation or as sunscreen compositions, they can be provided in the form of a suspension or dispersion in solvents or fatty substances, in the form of a non-ionic vesicular dispersion, or in the form of an emulsion, preferably of oil-in-water type, such as a cream or a milk, in the form of an ointment, gel, cream gel, solid tube, stick, aerosol foam or spray.

When the cosmetic compositions according to the invention are used for the photoprotection of the hair, that can be provided in the form of a shampoo, lotion, gel, emulsion or non-ionic vesicular dispersion and can constitute, for example, a rinse-out composition, to be applied before or after shampooing, before or after dyeing or bleaching and before, during or after permanent-waving or hair straightening, a styling or treating lotion or a styling or treating gel, a lotion or a gel for blow drying or hair setting, or a composition for permanent-waving or straightening, dyeing or bleaching the hair.

When the subject compositions are used as a product for making up the eyelashes, eyebrows or skin, such as a treatment cream for the epidermis, foundation, lipstick, eyeshadow, face powder, mascara or eyeliner, they can be provided in the anhydrous or aqueous, pasty or solid form, such as oil-in-water or water-in-oil emulsions, non-ionic vesicular dispersions, or suspensions.

For example, for the antisun/sunscreen formulations in accordance with the invention which comprise a vehicle of oil-in-water emulsion type, the aqueous phase (comprising in particular the hydrophilic screening agents) generally constitutes from 50% to 95% by weight, preferably from 70% to 90% by weight, with respect to the total weight of the formulation, the oily phase (comprising in particular the lipophilic screening agents) from 5% to 50% by weight, preferably from 10% to 30% by weight, with respect to the total weight of the formulation, and the (co)emulsifier(s) from 0.5% to 20% by weight, preferably from 2% to 10% by weight, with respect to the total weight of the formulation.

As hereinbefore indicated, the present invention also features a regime/regimen for the cosmetic treatment of the skin or hair, to protect these against the deleterious effects of UV radiation, comprising topically applying onto the skin or hair, an effective amount of a subject cosmetic composition.

In order to further illustrate the present invention and the advantages thereof, the following specific examples are given, it being understood that same are intended only as illustrative and in nowise limitative.

In said examples to follow, all parts and percentages are given by weight.

The following three (3) compositions were formulated via conventional cosmetic technique.

EXAMPLE 1

| COMPOSITION | Example 1 |
| --- | --- |
| 80/20 Mixture of cetearyl alcohol and of oxyethylenated (33 EO) cetearyl alcohol (Sinnowax AO, Henkel) | 7 g |
| Mixture of glycerol mono- and distearate (Cerasynt SD-V, ISP) | 2 g |
| Cetyl alcohol | 1.5 g |
| Polydimethylsiloxane (Dow Corning 200 Fluid, Dow Corning) | 1 g |
| Benzoate of $C_{12}/C_{15}$ alcohols (Witconol TN, Witco) | 15 g |
| 2,4-Bis{[4-(2-ethylhexyloxy)-2-hydroxy]-phenyl}-6-(4-methoxyphenyl)-1,3,5-triazine | 2 g |
| Benzotriazole silicone of formula (I') in which: r = 0, s = 1 and $$D = -CH_2-CH(CH_3)-CH_2-$$ | 3 g |
| Glycerol | 15 g |
| 1,4-Bis(benzimidazolyl)phenylene-3,3',5,5'-tetrasulfonic acid | 2 g |
| Triethanolamine | q.s. pH 7 |
| Preservatives | q.s. |
| Demineralized water, q.s. for | 100 g |

EXAMPLE 2

| COMPOSITION | Example 2 |
| --- | --- |
| Glycerol mono/distearate/polyethylene glycol (100 EO) stearate mixture (Arlacel 165 FL, ICI) | 2 g |
| Stearyl alcohol (Lanette 18, Henkel) | 1 g |
| Palm oil stearic acid (Stearine TP, Stearinerie Dubois) | 2.5 g |
| Polydimethylsiloxane (Dow Corning 200 Fluid, Dow Corning) | 0.5 g |
| Benzoate of $C_{12}/C_{15}$ alcohols (Witconol TN, Witco) | 20 g |
| Triethanolamine | 0.5 g |
| 2,4-Bis{[4-(tris(trimethylsiloxy)silyl-propyloxy)-2-hydroxy]phenyl}-6-(4-methoxy-phenyl)-1,3,5-triazine | 2.5 g |
| Benzotriazole silicone of formula (I') in which: r = 0, s = 1 and $$D = -CH_2-CH(CH_3)-CH_2-$$ | 2.5 g |
| Glycerol | 5 g |
| Hexadecyl phosphate, potassium salt (Amphisol K, Hoffman-Laroche) | 1 g |
| Polyacrylic acid (Synthalen K, 3V) | 0.3 g |
| Hydroxypropyl methyl cellulose (Methocel F4M, Dow Chemical) | 0.1 g |
| 1,4-Bis(benzimidazolyl)phenylene-3,3',5,5'-tetrasulfonic acid | 1.5 g |
| Triethanolamine | q.s. pH 7 |
| Preservatives | q.s. |
| Demineralized water, q.s. for | 100 g |

EXAMPLE 3

| COMPOSITION | Example 3 |
| --- | --- |
| 80/20 Mixture of cetearyl alcohol and of oxyethylenated (33 EO) cetearyl alcohol (Sinnowax AO, Henkel) | 7 g |
| Mixture of glycerol mono- and distearate (Cerasynt SD-V, ISP) | 2 g |
| Cetyl alcohol | 1.5 g |
| Polydimethylsiloxane (Dow Corning 200 Fluid, Dow Corning) | 1 g |
| Benzoate of $C_{12}/C_{15}$ alcohols (Witconol TN, Witco) | 15 g |
| 2,4-Bis{[4-(1',1',1',3',5',5',5'-hepta-methyltrisiloxy-2''-methylpropyloxy)-2-hydroxy]phenyl}-6-(4-methoxyphenyl)-1,3,5-triazine | 2 g |
| Benzotriazole silicone of formula (I') in which: r = 0, s = 1 and $$D = -CH_2-CH(CH_3)-CH_2-$$ | 3 g |
| Glycerol | 15 g |
| 1,4-Bis (benzimidazolyl) phenylene-3,3',5,5'-tetrasulfonic acid | 1.5 g |
| Triethanolamine | q.s. pH 7 |
| Preservatives | q.s. |
| Demineralized water, q.s. for | 100 g |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable sunscreen/cosmetic composition suited for the photoprotection of human skin and/or hair, comprising synergistically effective amounts of each of (a) at least one benzotriazole compound having the structural formula (I):

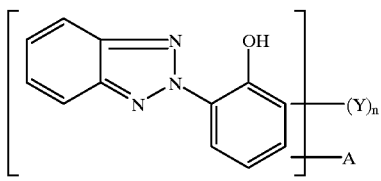

(I)

in which A is a hydrogen atom or a divalent radical —L—W—; n has the value 1, 2 or 3; the radicals Y, which may be identical or different, are each a $C_1$–$C_{10}$ alkyl radical, a halogen atom, a $C_1$–$C_{10}$ alkoxy radical, or a sulfo group, with the proviso that, in the latter case, two adjacent Y radicals on the same aromatic nucleus may together form an alkylidenedioxy radical in which the alkylidene moiety was 1 or 2 carbon atoms, also with the proviso that the Y radicals are other than a sulfo group when A is other than a hydrogen atom; L is a divalent radical of the following formula (II):

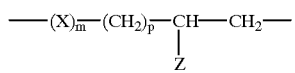

(II)

in which X is O or NH; Z is a hydrogen atom or a $C_1$–$C_4$ alkyl radical; n is an integer ranging from 0 to 3, inclusive; m is 0 or 1; p is an integer ranging from 1 to 10 inclusive; W is a radical of the following formula (1), (2) or (3):

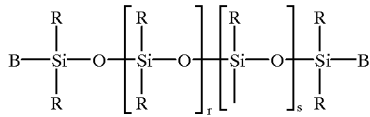

(1)

or

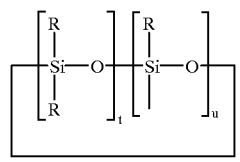

(2)

or

(3)

in which formulae the radicals R, which may be identical or different, are each a $C_1$–$C_{10}$ alkyl radical, phenyl or 3,3,3-trifluoro-propyl radical, at least 80% by number of the R radicals being methyl radicals; the radicals B, which may be identical or different, are each an R radical or the V radical of the following formula:

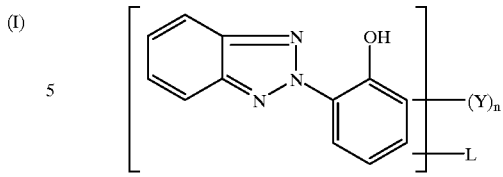

in which Y, n and L are as defined above; r is an integer ranging from 0 to 50, inclusive, and s is an integer ranging from 1 to 20, inclusive, and, if s=0, at least one of the two B radicals is a radical V; u is an integer ranging from 1 to 6, inclusive, and t is an integer ranging from 0 to 10, inclusive, with the proviso that t+u is equal to or greater than 3; (b) at least one bisresorcinyltriazine compound; and (c) at least one compound containing at least two benzoazolyl functional groups per molecule or at least one compound containing, per molecule, at least one benzodiazolyl functional group, formulated into a topically applicable, cosmetically acceptable vehicle, diluent or carrier therefor.

2. The sunscreen/cosmetic composition as defined by claim 1, wherein the compounds of formula (I) are selected from the group consisting of 2-(2'-hydroxy-5'-methylphenyl)benzotriazole; 2-(2'-hydroxy-3'-butyl-5'-methylphenyl)benzotriazole; 2-(2'-hydroxy-5'-(t-octyl)phenyl)benzotriazole; and 2-(2'-hydroxy-3'-(sec-butyl)-5'-sulfophenyl)-benzotriazole.

3. The sunscreen/cosmetic composition as defined by claim 1, wherein the benzotriazole compound of formula (I) is selected from among those in which A is a divalent radial —L—W— and W has the structure of formula (1) and at least one of the following conditions is satisfied:

R is alkyl and, r ranges from 0 to 15, inclusive; s ranges from 1 to 5, inclusive, n is not zero and Y is methyl, tert-butyl or $C_1$–$C_4$ alkoxy, Z is hydrogen or methyl, m=0 or [m=1 and X=O], p is equal to 1.

4. The sunscreen/cosmetic composition as defined by claim 3, all of said conditions being satisfied.

5. The sunscreen/cosmetic composition as defined by claim 1, said at least one benzotriazole compound having the structural formula (I'):

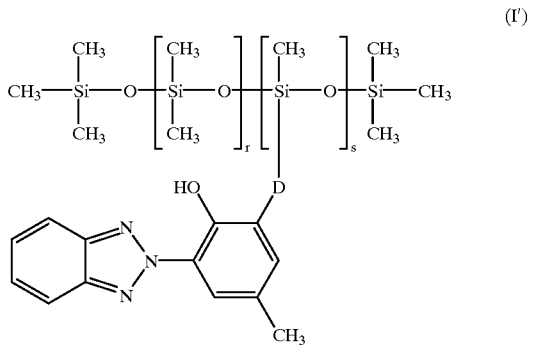

(I')

in which $0 \leq r \leq 15$; $1 \leq s \leq 5$; and D is a divalent radical:

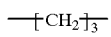    or    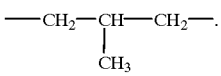

6. The sunscreen/cosmetic composition as defined by claim 5, said at least one benzotriazole compound having the structural formula (I') in which r=0; s=1; and

D = —CH$_2$—CH(CH$_3$)—CH$_2$.

7. The sunscreen/cosmetic composition as defined by claim 5, said at least one benzotriazole compound having the structural formula (I') in which r=0; s=1; and

D=—[—CH$_2$—]$_3$—

8. The sunscreen/cosmetic composition as defined by claim 1, comprising from 0.1% to 15% by weight of said at leastd one benzotriazole compound.

9. The sunscreen/cosmetic composition as defined by claim 8, as defined by comprising from 0.2% to 10% by weight of said at least one benzotriazole compound.

10. The sunscreen/cosmetic composition as defined by claim 1, said at least one bisresorcinyltriazine compound having the following structural formula:

(III)

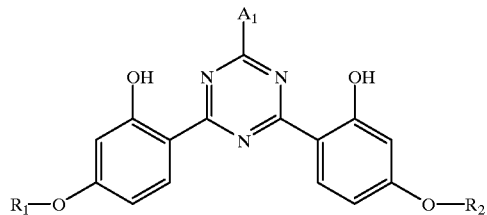

in which (i) the $R_1$ and $R_2$ radicals, which may be identical or different, are each a $C_3$–$C_{18}$ alkyl radical, a $C_2$–$C_{18}$ alkenyl radical, or a residue of formula —CH$_2$—CH(OH)—CH$_2$—OT$_1$ wherein T$_1$ is a hydrogen atom or a $C_1$–$C_8$ alkyl radical; or (ii) the $R_1$ and $R_2$ radicals, which again may be identical or different, are also each a residue of the following formula (4):

(4)

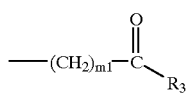

in which m$_1$ is a number ranging from 1 to 3; R$_3$ is a hydroxyl group, a $C_1$–$C_5$ alkyl radical which is unsubstituted or substituted by one or more hydroxyl groups, a $C_1$–$C_5$ alkoxy radical, an amino group, a mono- or di($C_1$–$C_5$)alkylamino radical, a metal cation M, or a residue having one of the following formulae (5) to (10):

(5)

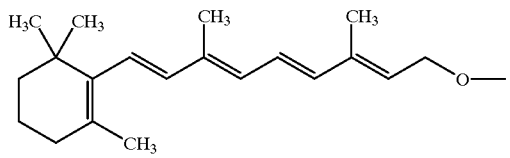

(6)

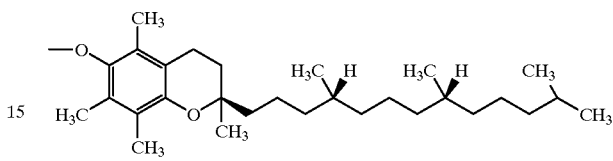

(7)

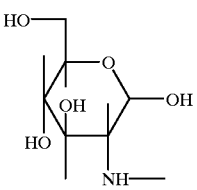

(8)

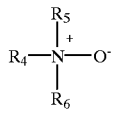

(9)

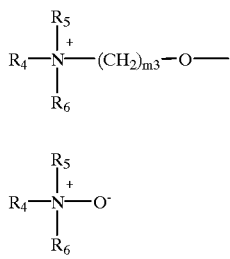

(10)

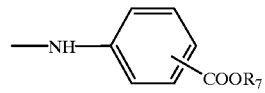

in which the $R_4$, $R_5$ and $R_6$ radicals, which may be identical or different, are each a $C_1$–$C_{14}$ alkyl radical which is unsubstituted or substituted by one or more hydroxyl groups; $R_7$ is a hydrogen atom, a metal cation M, a $C_1$–$C_5$ alkyl radical, or a residue of formula —(CH$_2$)$_{m2}$—OT$_1$ wherein m$_2$ is a number ranging from 1 to 4 and T$_1$ is as defined above; or (iii) the $R_1$ and $R_2$ radicals, which again may be identical or different, are also each a residue of the following formula (11):

(11)

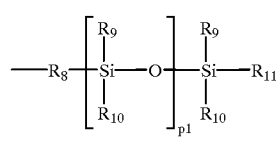

in which R$_8$ is a covalent bond, a linear or branched $C_1$–$C_4$ alkyl radical, or a residue of formula —C$_{m4}$H$_{2m4}$—C$_{m4}$H$_{2m4}$—O— wherein m$_4$ is a number ranging from 1 to 4; p$_1$ is a number ranging from 0 to 5; the R$_9$, R$_{10}$ and R$_{11}$ radicals, which may be identical or different, are each a $C_1$–$C_{18}$ alkyl radical, a $C_1$–$C_{18}$ alkoxy radical, or a residue of the formula:

(12)

$$-\!\!-\!\!O-\!\!\underset{\underset{R_{12}}{|}}{\overset{\overset{R_{12}}{|}}{Si}}-\!\!R_{12}$$

wherein $R_{12}$ is a $C_1$–$C_5$ alkyl radical; $A_1$ is a residue corresponding to one of the following formulae:

(10)

[structure: —NH—C6H4—COOR7]

(13)

[structure: methyl-phenyl—OR13]

(14)

[structure: N-pyrrole with Q1 substituent and methyl]

(15)

[structure: HO—phenyl(methyl)—OR14]

in which $R_7$ is as defined above; $R_{13}$ is a hydrogen atom, a $C_1$–$C_{10}$ alkyl radical, a radical of formula —(CH$_2$CHR$_{16}$—O)$_{n1}$R$_7$ wherein $n_1$ is a number ranging from 1 to 16 and $R_{16}$ is a hydrogen atom or a methyl radical, or a residue of formula —CH$_2$—CH(OH)—CH$_2$OT$_1$ wherein $T_1$ is as defined above; $Q_1$ is a $C_1$–$C_{18}$ alkyl radical; $R_{14}$ is a radical having the formula (4):

(4)

$$-\!\!-\!\!(CH_2)_{m1}\!\!-\!\!\overset{\overset{O}{\|}}{C}\!\!-\!\!R_3$$

as defined above.

11. The sunscreen/cosmetic composition as defined by claim 10, said at least one compound of formula (III) comprising:
(1) those in which the Al radical is para-methoxyphenyl or para-ethoxyphenyl and the $R_1$ and $R_2$ radicals, which may be identical or different, are each a radical having the structure:

$$-\!\!-\!\!(CH_2)\!\!-\!\!\overset{\overset{O}{\|}}{C}\!\!-\!\!R_3$$

in which $R_3$ is selected from among:
tert-butyloxy;
OH;
OM, wherein M is an alkali metal or alkaline earth metal cation, or a cation selected from among copper, magnesium or zinc;

a group having the structure:

[structure: —NH—C6H4—COOC4H9]

a group having the structure O$^-$N$^+$(CH$_2$CH$_2$OH)$_3$;
a group having the structure:

$$H_3C-\!\!\underset{\underset{CH_3}{|}}{\overset{\overset{CH_3}{|}}{\overset{+}{N}}}\!\!-\!\!(CH_2)n O-\!\!-$$

wherein n ranges from 2 to 16;
a group having the structure:

[structure: HO—CH(—)—CH(OH)—CH3 type, propanediol fragment]

or a group having the structure:

[structure: retinyl methyl ether type polyene with trimethylcyclohexenyl group]

or (2) or those in which the $A_1$ radical is para-hydroxyphenyl and the $R_1$ and $R_2$ radicals simultaneously are each a group having the structure:

$$HO-\!\!\overset{\overset{O}{\|}}{C}\!\!-\!\!CH_2-\!\!-.$$

12. The sunscreen/cosmetic composition as defined by claim 10, said at least one compound of formula (III) being selected from the group consisting of: 2,4-bis{[4-(2-ethylhexyloxy)-2-hydroxy]phenyl}-6-(4-methoxyphenyl)-1,3,5-triazine; 2,4-bis{[4-(3-(2-propyloxy)-2-hydroxypropyloxy)-2-hydroxy]phenyl}-6-(4-methoxyphenyl)-1,3,5-triazine; 2,4-bis{[4-(2-ethylhexyloxy)-2-hydroxy]phenyl}-6-[4-(2-methoxyethyloxycarbonyl)phenylamino]-1,3,5-triazine; 2,4-bis{[4-(tris(trimethylsiloxy)silylpropyloxy)-2-hydroxy]phenyl}-6-(4-methoxyphenyl)-1,3,5-triazine; 2,4-bis{[4-(2"-methylpropenyloxy)-2-hydroxy]phenyl}-6-(4-methoxyphenyl)-1,3,5-triazine; 2,4-bis{[4-(1', 1', 1', 3', 5', 5', 5'-heptamethyltri-siloxy-2"-methylpropyloxy)-2-hydroxy]phenyl}-6-(4-methoxyphenyl)-1,3,5-triazine; 2,4-bis{[4-(3-(2-propyloxy)-2 -hydroxypropyloxy)-2-hydroxy]phenyl}-6-[4-(ethoxycarbonyl)phenylamino]-1,3,5-triazine; and 2,4-bis{[4-(2-ethylhexyloxy)-2-hydroxy]phenyl}-6-(1-methylpyrrol-2-yl)-1,3,5-triazine.

13. The sunscreen/cosmetic as defined by claim 12, said at least one compound of formula (III) being selected from the group consisting of 2,4-bis{[4-(2-ethylhexyloxy)-2-hydroxy]phenyl}-6-(4-methoxyphenyl)-1,3,5-triazine; 2,4-bis{[4-(tris(trimethylsiloxy)silylpropyloxy)-2-hydroxy]phenyl}-6-(4-methoxyphenyl)-1,3,5-triazine; and 2,4-bis{

[4-(1', 1', 1', 3', 5', 5', 5'-heptamethyltrisiloxy-2"-methylpropyloxy)-2-hydroxy]phenyl}-6-(4-methoxyphenyl)-1,3,5-triazine.

14. The sunscreen/cosmetic composition as defined by claim 1, comprising from 0.1% to 15% of said at least one bisresorcinyltriazine compound.

15. The sunscreen/cosmetic composition as defined by claim 14, comprising from 0.2% to 10% by weight of said at least one bisresorcinyltriazine compound.

16. The sunscreen/cosmetic composition as defined by claim 1, comprising at least one compound containing at least two benzoazolyl groups and having the following structural formula (IV):

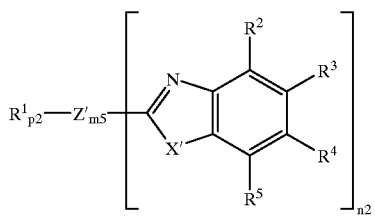

(IV)

in which Z' is an organic residue having a valency of $(p_2+n_2)$ comprising one or more double bonds which are positioned such that the double bond completes the system of double bonds of at least two benzoazolyl groups as defined inside the brackets, in order to form a completely conjugated structural unit; X' is S, O or $NR^6$; $R^1$ is a hydrogen atom, a $C_1$–$C_{18}$ alkyl radical, a $C_1$–$C_4$ alkoxy radical, a $C_5$–$C_{15}$ aryl radical, a $C_2$–$C_{18}$ acyloxy radical, $SO_3Y'$ or $COOY'$; the $R^2$, $R^3$, $R^4$ and $R^5$ radicals, which may be identical or different, are each a nitro group or a radical $R^1$; $R^6$ is a hydrogen atom, a $C_1$–$C_4$ alkyl radical, or a $C_1$–$C_4$ hydroxyalkyl radical; Y' is a hydrogen atom, Li, Na, K, $NH_4$, 1/2Ca, 1/2Mg, 1/3Al, or a cation resulting from the neutralization of a free acid group by a nitrogenous organic base; $m_5$ is 0 or 1; $n_2$ is a number ranging from 2 to 6; $p_2$ is a number ranging from 1 to 4; with the proviso that $p_2+n_2$ does not exceed the value 6.

17. The sunscreen/cosmetic composition as defined by claim 16, wherein formula (IV) the radical is selected from the group consisting of:

(a) an unsaturated linear aliphatic $C_2$–$C_6$ hydrocarbonaceous radical which can be interrupted by a $C_5$–$C_{12}$ radical group or a $C_4$–$C_{10}$ heteroaryl radical, (b) a $C_5$–$C_{15}$ aryl radical which can be interrupted by an unsaturated linear aliphatic $C_2$–$C_6$ hydrocarbonaceous radical; and (c) a $C_3$–$C_{10}$ heteroaryl radical, with the proviso that the Z' radical may be substituted by $C_1$–$C_6$ alkyl, $C_1$–$C_6$ alkoxy, phenoxy, hydroxyl, methylenedioxy or amino radicals, the amino radicals optionally being substituted by one or 2 $C_1$–$C_5$ alkyl radicals.

18. The sunscreen/cosmetic composition as defined by claim 16, wherein formula (IV) the Z radical is selected from the group consisting of:

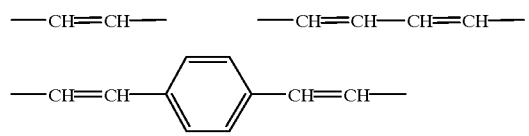

-continued

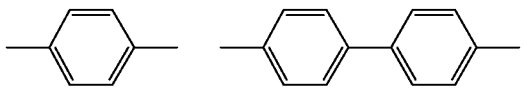

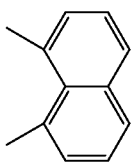
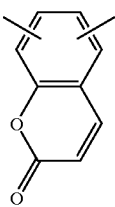

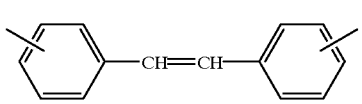

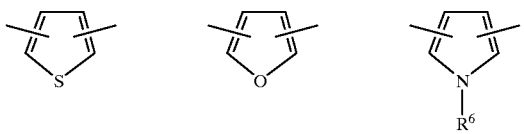

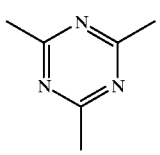

19. The sunscreen/cosmetic composition as defined by claim 16, said at least one compound having the formula (IV) being selected from among the following compounds or salt thereof:

Compound 1

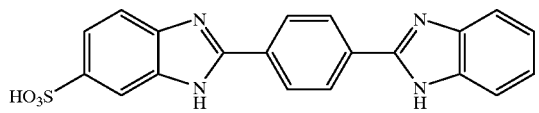

Compound 2

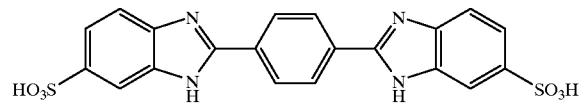

Compound 3

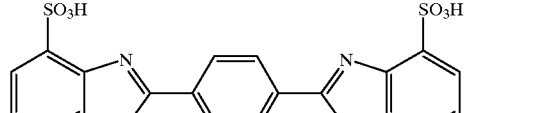

Compound 4

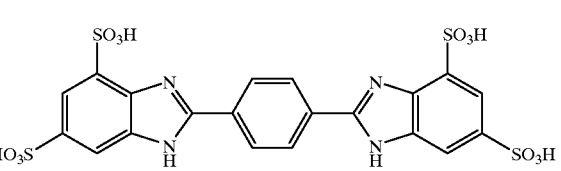

-continued
Compound 5
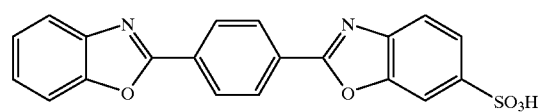
Compound 6
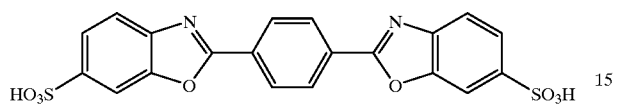
Compound 7
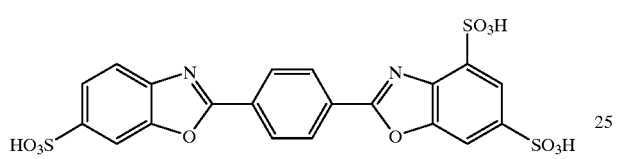
Compound 8
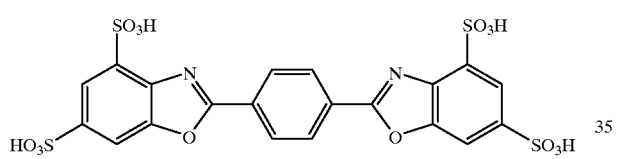
Compound 9
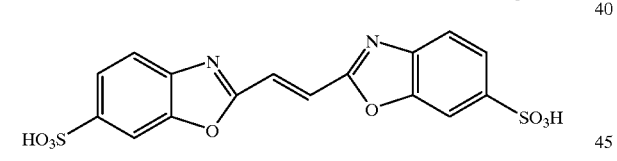
Compound 10
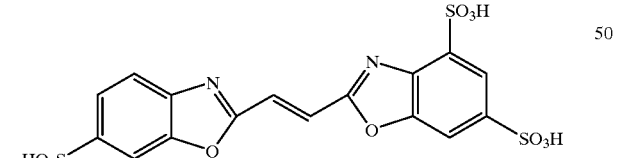
Compound 11
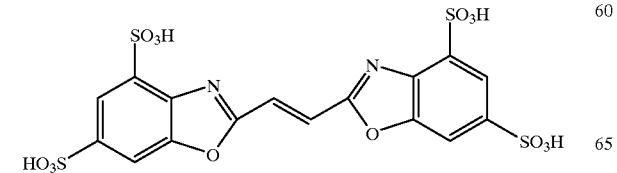
-continued
Compound 12
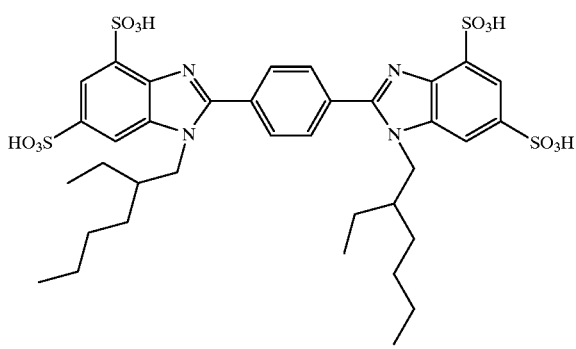
Compound 13
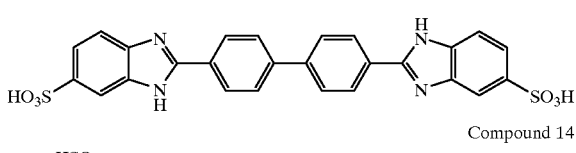
Compound 14
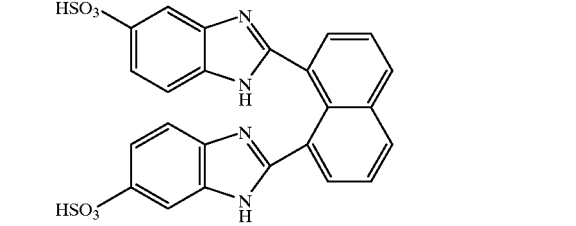
Compound 15
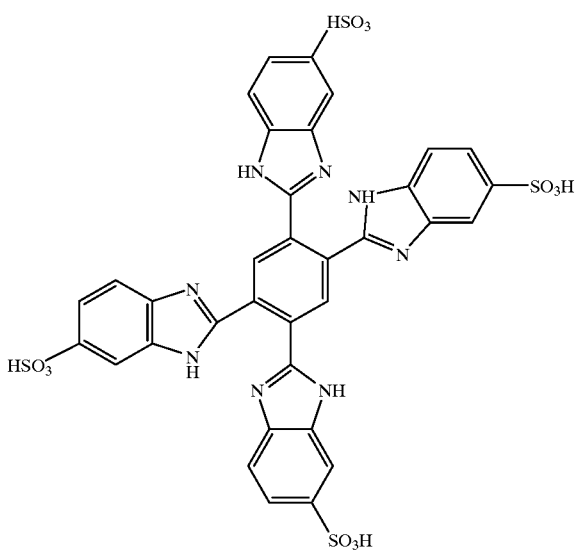
Compound 16
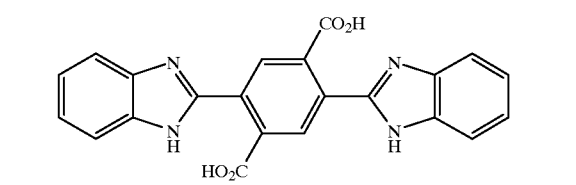

-continued

Compound 17
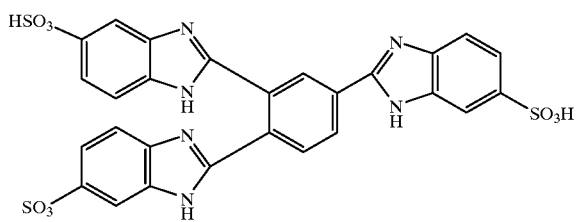

Compound 18
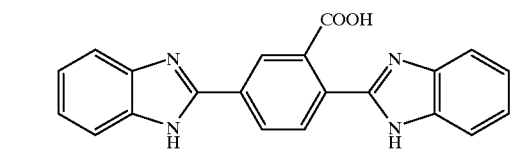

Compound 19
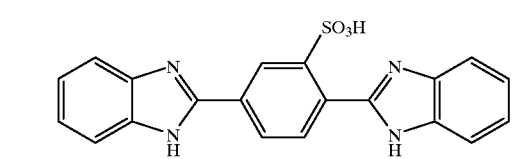

Compound 20
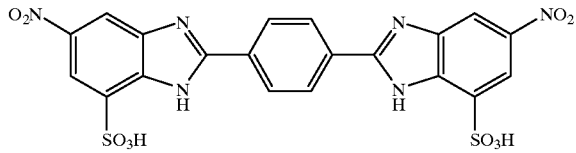

Compound 21
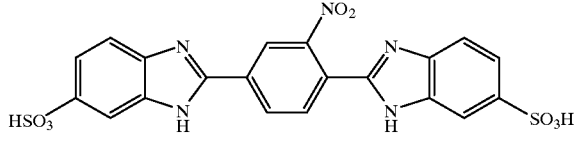

Compound 22
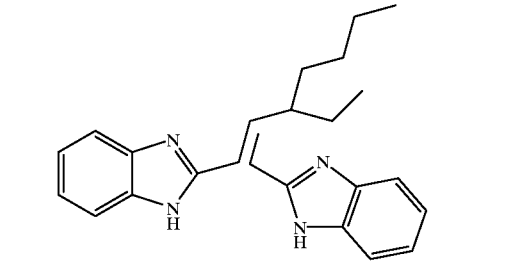

Compound 23
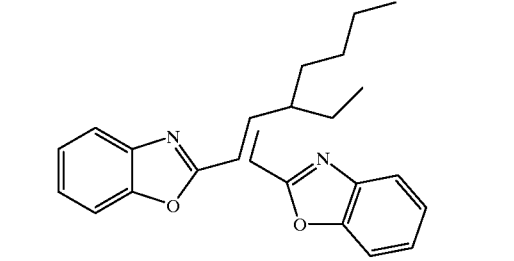

-continued

Compound 24
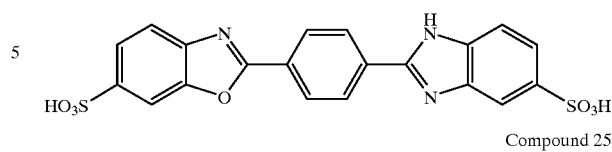

Compound 25
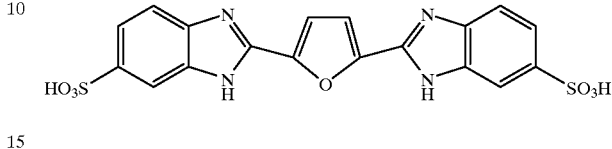

Compound 26
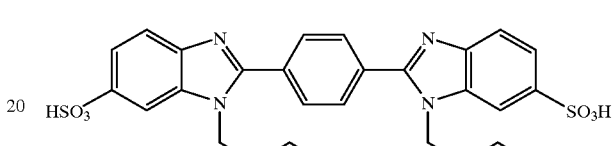

Compound 27
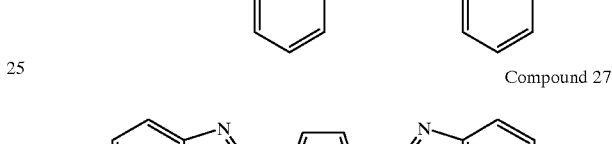

20. The sunscreen/cosmetic composition as defined by claim 16, said at least one compound of formula (IV) comprising 1,4-bis(benzimidazolyl)phenylene-3,3', 5,5'-tetra-sulfonic acid or salt thereof and having the following formula:

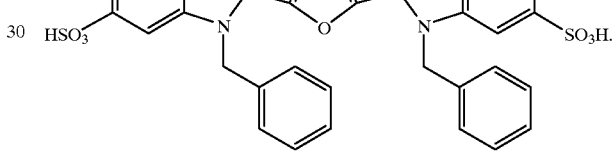

21. The sunscreen/cosmetic composition as defined by claim 1, comprising at least one compound containing at least two benzoazolyl groups or salt thereof selected from among:

Compound 28
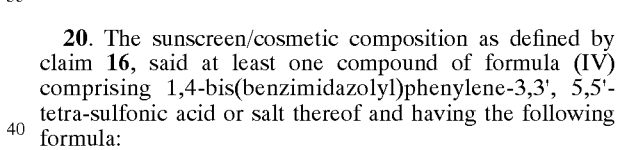

Compound 29
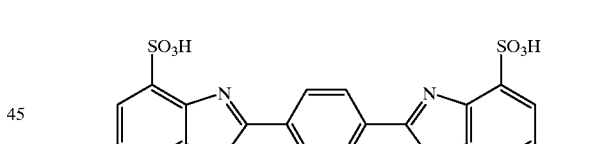

Compound 30

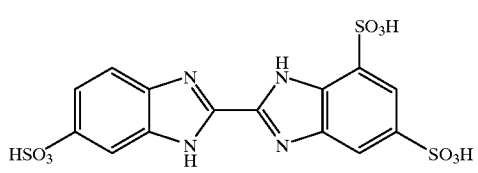

Compound 31

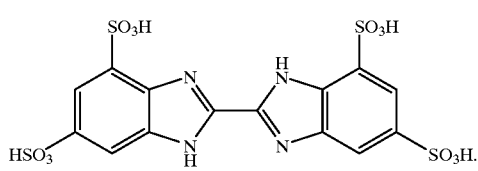

22. The sunscreen/cosmetic composition as defined by claim 1, comprising at least one compound containing at least one benzodiazolyl group or salt thereof selected from among:

Compound 32

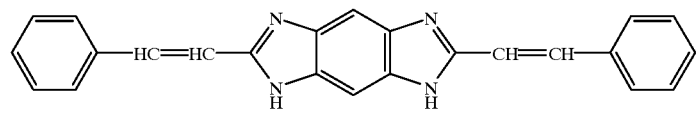

Compound 33

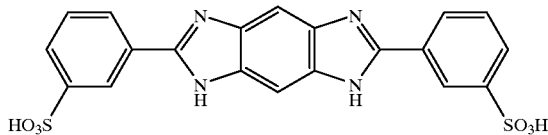

Compound 34

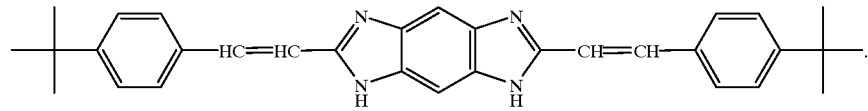

23. The sunscreen/cosmetic composition as defined by claim 1, comprising benzoazolyl or benzodiazolyl groups are comprising from 0.1% to 15% by weight of said at least one benzoazolyl/benzodiazolyl compound.

24. The sunscreen/cosmetic composition as defined by claim 23, comprising from 0.2% to 10% by weight of said at least one benzoazolyl/benzodiazolyl compound.

25. The sunscreen/cosmetic composition as defined by claim 1, formulated as an oil-in-water emulsion.

26. The sunscreen/cosmetic composition as defined by claim 1, formulated as a water-in-oil emulsion.

27. The sunscreen/cosmetic composition as defined by claim 1, further comprising at least one additional hydrophilic or lipophilic organic UV-A and/or UV-B sunscreen.

28. The sunscreen/cosmetic composition as defined by claim 27, further comprising at least one cinnamic derivative, salicylic derivative, camphor derivative, triazine derivative, benzophenone derivative, dibenzoylmethane derivative, benzimidazole derivative, β-β-diphenylacrylate derivative, p-aminobenzoic acid derivative, sunscreen polymer, or sunscreen silicone.

29. The sunscreen/cosmetic composition as defined by claim 1, further comprising a photoprotecting effective amount of particulates of at least one coated or uncoated inorganic pigment or nanopigment.

30. The sunscreen/cosmetic composition as defined by claim 29, said at least one pigment or nanopigment comprising titanium dioxide, zinc oxide, iron oxide, zirconium oxide, cerium oxide, or mixture thereof.

31. The sunscreen/cosmetic composition as defined by claim 1, further comprising at least one active agent for the artificial tanning and/or browning of human skin.

32. The sunscreen/cosmetic composition as defined by claim 1, further comprising at least one cosmetically acceptable adjuvant or additive.

33. The sunscreen/cosmetic composition as defined by claim 32, said at least one adjuvant or additive comprising a fat, organic solvent, thickening agent, softener, antioxidant, opacifying agent, stabilizing agent, emollient, hydroxy acid, anti-foaming agent, hydrating agent, vitamin, fragrance, preservative, surfactant, filler, sequestering agent, polymer, propellant, basifying or acidifying agent, dye, colorant, or mixture thereof.

34. The sunscreen/cosmetic composition as defined by claim 1, comprising a nonionic vesicle dispersion, emulsion, cream, milk, gel, cream gel, ointment, suspension, dispersion, powder, solid stick or tube, foam or spray.

35. The sunscreen/cosmetic composition as defined by claim 1, comprising a makeup.

36. The sunscreen/cosmetic composition as defined by claim 35, comprising an anhydrous or aqueous solid or paste, emulsion, suspension, or dispersion.

37. The sunscreen/cosmetic composition as defined by claim 1, comprising a shampoo, lotion, gel, nonionic vesicle dispersion, hair lacquer, or rinse.

38. The sunscreen/cosmetic composition as defined by claim 1, having a sun protection factor of at least 2.

39. A regime/regimen for protecting human skin and/or hair against the deleterious effects of ultraviolet irradiation, comprising topically applying thereto an effective amount of the sunscreen/cosmetic composition as defined by claim 1.

40. A regime/regimen for protecting human skin and/or hair against the deleterious effects of solar radiation, comprising topically applying thereto a effective amount of the sunscreen/cosmetic composition as defined by claim 1.

* * * * *